United States Patent [19]
Randolph

[11] Patent Number: 6,086,368
[45] Date of Patent: Jul. 11, 2000

[54] PORTABLE AIR-DRIVEN DENTAL APPARATUS AND METHODS

[76] Inventor: Robert G. Randolph, 4146 Howard Ave., Western Springs, Ill. 60558

[21] Appl. No.: 09/176,005

[22] Filed: Oct. 20, 1998

[51] Int. Cl.$^7$ .................................................. B05B 9/04
[52] U.S. Cl. .............................................. 433/101; 433/84
[58] Field of Search ............................... 433/98, 99, 100, 433/101, 84

[56] References Cited

U.S. PATENT DOCUMENTS

| | | | |
|---|---|---|---|
| 525,816 | 9/1894 | Osborn | 433/84 |
| 727,736 | 5/1903 | Basford | 433/84 |
| 1,080,261 | 12/1913 | Bush | 433/84 |
| 3,553,840 | 1/1971 | Bordelon | 433/98 |
| 4,286,949 | 9/1981 | Holt, Jr. | 433/101 |
| 5,013,240 | 5/1991 | Bailey et al. | 433/98 |
| 5,211,558 | 5/1993 | Bailey et al. | 433/98 |

*Primary Examiner*—Todd E. Manahan
*Attorney, Agent, or Firm*—Solomon Zaromb

[57] ABSTRACT

A portable dental apparatus for treating patients or animals in remote locations comprises a dental drill driven by an air turbine; a pressurized air supply for driving the turbine and for pressurizing a water supply; and connections and valving for operating the drill and cooling it with a stream of water from the water supply and for squirting air or water from the air and water supplies with a squirt nozzle. Tile pressurized air supply derives its air from manual pumping, preferably with a double-action pump and a check valve to minimize fluctuations in the air flow rate. Such a pump either forms part of the air supply or is used to fill an inflatable container. The air supply may consist of the inflatable container alone, or of one or two double-action pumps, or of the container and one pump. The water supply comprises a can having a capped opening at or near its top for filling with water when needed, a tubule extending from its inside near its base to above its top, and a threaded opening in or near its base into which is screwed an adapter that can be either plugged or used to enlarge the capacity of the water supply. The apparatus also comprises quick disconnect and connect tubing between the air supply, valving, water supply, drill, and squirting nozzle to facilitate its assembly and disassembly.

18 Claims, 3 Drawing Sheets

PORTABLE AIR-DRIVEN DENTAL APPARATUS AND METHODS

BACKGROUND OF THE INVENTION

This invention relates to dental instruments for operation in remote locations, and especially to portable instruments. My invention has particular application to the practice of dentistry in underdeveloped regions and also to veterinary dentistry. More specifically, the invention relates to portable air-driven dental drilling and bone cutting apparatus and methods.

The air-driven dental apparatus that is disclosed herein has been successfully tested for treating patients of the Huaorani tribe in the Amazon jungles of Ecuador. Its major components can be readily disassembled, so that they can fit within a compact hand-carried case, and be readily reassembled for use when needed.

Current dental procedures for remote locations, as prescribed by the World Health Organization, call for purely manual operations, without recourse to a dental drill. Such operations preclude silver fillings and other treatments that may necessitate drilling or cutting of dental bones.

It is therefore the purpose of this invention to provide portable dental drilling equipment that will be practical and cost-effective for use in remote and impoverished regions.

Previously reported portable air-driven dental instruments require either a disposable or refillable compressed air container, such as those used by scuba divers, for their operation. Such containers have to be frequently replaced. The replacement costs of the disposable containers may be beyond the means of some impoverished populations in underdeveloped regions. The refillable containers require heavy and costly air compressors and electrical or internal-combustion-engine power, which are not usually available in remote and underdeveloped places. Also, the weight of these containers, when added to that of other needed supplies and equipment, makes it inconvenient to hand-carry the entire equipment to remote areas.

It is therefore another object of this invention to provide a dental drilling instrument that can operate without either electrical power or a compressed air tank.

The preferred embodiment of the invention disclosed herein usually requires the aid of one or two persons for operation during a dental treatment. This requirement presents no problem in most cases where there is plenty of manpower available. However, in veterinary dentistry, the readily available manpower may be needed to restrain a treated animal. It may then be desirable to have the ability to operate the equipment single-handedly.

It is therefore still another object of this invention to provide inexpensive and portable or easily transportable dental drilling equipment that can be operated preferably by a single person.

Other objects of the invention will become apparent to professionals in dentistry and related areas following perusal of the complete specification.

SUMMARY OF THE INVENTION

Briefly, the invention provides portable dental apparatus and methods for treating patients or animals in remote locations. The apparatus comprises a dental drill driven by an air turbine; a pressurized air supply for driving the turbine and for pressurizing a water supply; and connections and valving for operating the drill and cooling it with a stream of water from the water supply and for squirting air or water from the air and water supplies with a squirt nozzle. The pressurized air supply derives its air from manual pumping, preferably with a double-action pump and a check valve to minimize fluctuations in the air flow rate. Such a pump either forms part of the air supply or is used to fill an inflatable container. The air supply may consist of the inflatable container alone, or of one or two double-action pumps, or of the container and one pump. The water supply comprises a can having a capped opening at or near its top for filling with water when needed, a tubule extending from its inside near its base to above its top, and a threaded opening in or near its base into which is screwed an adapter that can be either plugged or used to enlarge the capacity of the water supply. The apparatus also comprises quick disconnect and connect tubing between the air supply, valving, water supply, drill, and squirting means to facilitate its assembly and disassembly. The disassembled apparatus can be fitted into a readily transportable carrying case.

Additional objects, advantages and novel features of the invention will be set forth in part in the description which follows, and in part will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention there are illustrated in the accompanying drawings preferred embodiments thereof, from an inspection of which, when considered in connection with the following description, the invention, its construction and operation, and many of its advantages should be readily understood and appreciated.

DESCRIPTION OF THE PREFERRED EMBODIMENTS

Figure 1:
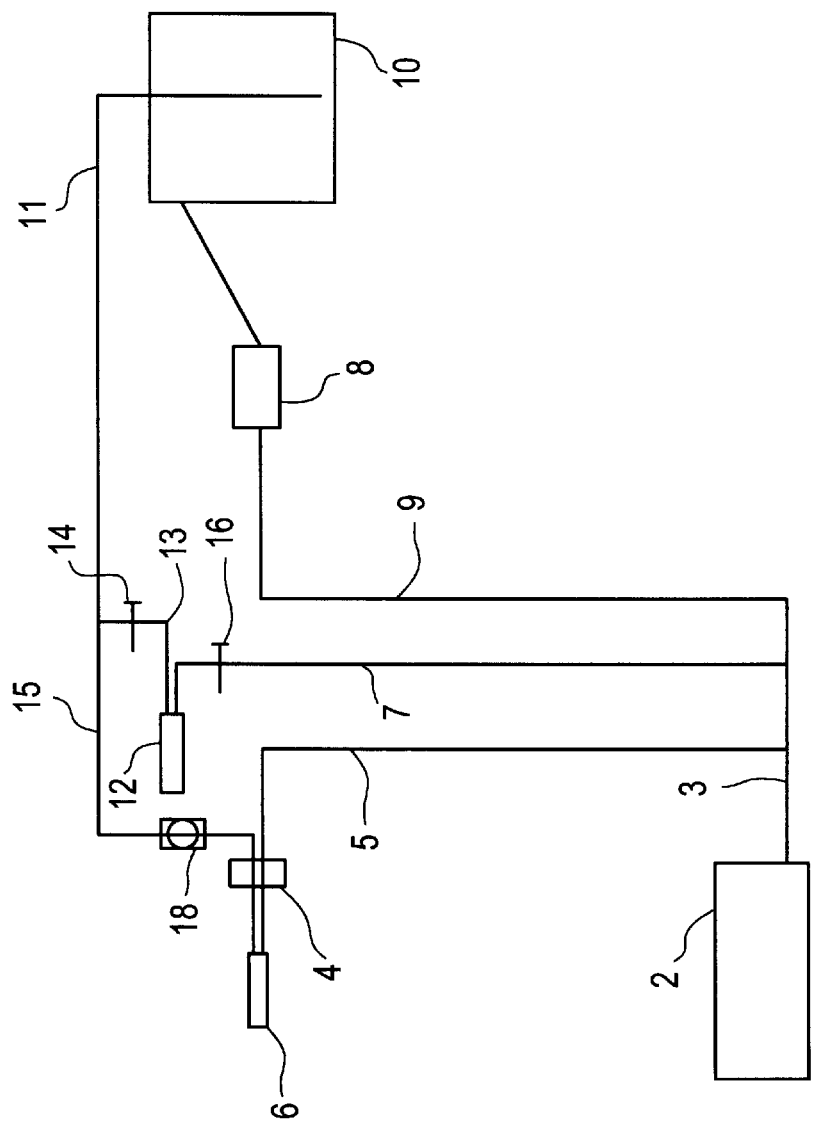
FIG. 1 is a schematic block diagram of the fluids flow components of the present invention.

Referring to FIG. 1, there is shown a schematic block diagram of the fluids flow system of a dental apparatus made in accordance with the present invention.

In operation, the air that is to drive the dental turbine of the dental drill 6 is supplied by a pressurized air source 2, to be described below, and is fed via a main compressed air line 3 into three branching pressurized lines 5, 7, and 9, which lead to the drill 6, a squirt nozzle 12, and a water supply 10, respectively. The air flow to drill 6 is controlled by a foot-pedal valve 4, whereas that to squirt nozzle 12 is actuated and adjusted by means of a push-button-controlled tire valve 16.

A check valve 8 in line 9 prevents water in the supply 10 from backing into the air line system. The pressurized air that is fed to the top of supply 10 forces water out through pressurized water line 11 into lines 13 and 15 which lead to the squirt nozzle 12 and the drill 6, respectively. A push-button-controlled valve 14 serves to actuate and adjust the water flow through nozzle 12. The water flow through drill 6, which removes the heat that is generated by the drilling action, is preferably a continuous stream whose rate can be adjusted by a needle valve or ball valve 18 and actuated by the foot pedal 4 simultaneously with the air flow. Alternatively, valve 18 may also serve to actuate the water flow through drill 6, with foot pedal 4 serving merely to control the air flow.

Figure 2:
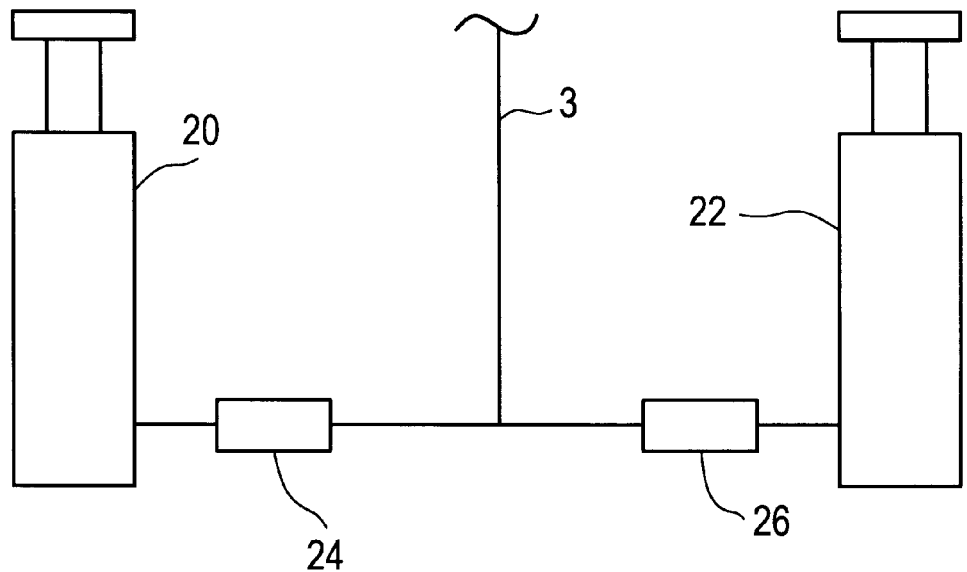
FIG. 2 is a schematic diagram of the pressurized air source 2 of FIG. 1 according to the preferred embodiment of the invention.
Figure 3:
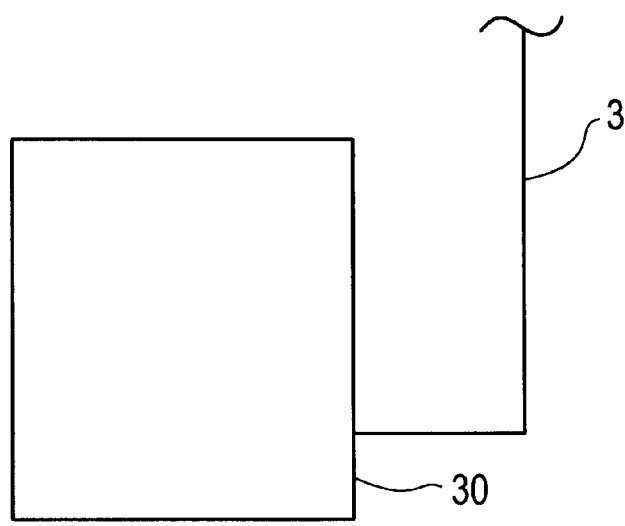
FIG. 3 is a schematic diagram of the air source 2 in an alternative embodiment of the invention.

The pressurized air source 2 of FIG. 1 may consist either of a manually operated air pump 20, as shown in FIG. 2, or of a pressurized inflatable container 30, e.g., a truck tire, as shown in FIG. 3. In the preferred embodiment of the invention, shown in FIG. 2, a manually operated double-action pump 20, which pushes compressed air into line 3 whether its piston is moving up or down, such as a tire pump Model "Big Blast" manufactured by Bell Sports, Rantoul, Ill., feeds air through a check valve 24 into the compressed air line 3, preferably at a pressure of about 45–70 psig [pounds/square inch gage] at a flow rate of about 3 cfm [cubic feet/minute]. The double action of pump 20 reduces fluctuations in the air flow through drill 6, especially in conjunction with check valve 24. To facilitate the pumping action, especially when a high flow rate is required to operate the air turbine during bone cutting, a second optional pump 22 with check valve 26 may be added on and connected to line 3 by a Y- or T-junction, as shown in FIG. 2. This embodiment meets the needs of dentists practicing among indigenous populations in remote areas where manpower is plentiful while provisions are scarce.

Nevertheless, it may be desirable under certain circumstances for a dentist to be able to operate the equipment without having to rely on auxiliary manpower. For instance, in veterinary dentistry, all the available help may have to concentrate on restraining an animal that is undergoing dental treatment.

The alternative embodiment of the invention shown in FIG. 3 is intended to meet such a need. Here, an inflatable container 30, e.g., a large truck tire, is connected to the compressed air line 3 in lieu of the pump 20 of FIG. 2. Container 30 can be inflated prior to each dental treatment to a pressure of about 70 psig using the hand pump 20, after which the container is connected to line 3, as shown in FIG. 3, for operation of the dental equipment.

In another alternative embodiment of the invention, the inflated container 30 of FIG. 3 may replace the second pump 22 of FIG. 2, thereby facilitating the pumping by one person without the help of yet another person.

Although an inflatable container of the required size may be too heavy and bulky to be readily portable, it is possible to adapt it so as to have it serving as a transportation aid. For instance, a truck tire can be provided with an axle, handle, and carrier means [not shown] so that it could carry needed equipment and supplies as it is being wheeled from one location to another.

The foregoing explained the operation of the pressurized air system according to this invention. To explain the operation of the associated pressurized water system, reference is made to the water supply 10 of FIG. 1, as shown in more detail in FIGS. 4 and 5.

Figure 4:
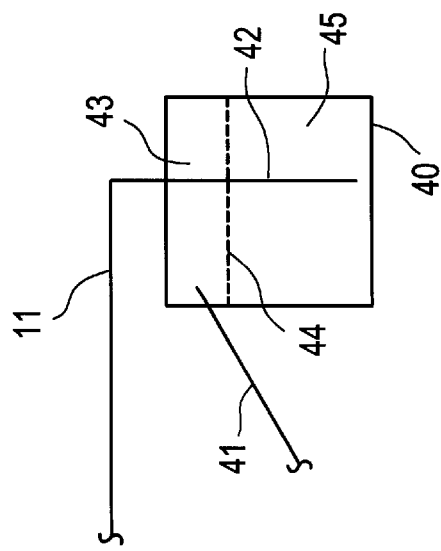
FIG. 4 is a schematic diagram showing the simplest variant of the water supply 10 of FIG. 1.

In FIG. 4, the water supply 10 of FIG. 1 comprises a water can 40 that is partly filled with water up to the liquid level 44. Compressed air from line 9 of FIG. 2 is injected above level 44 so as to pressurize the can, which causes part of the pressurized water to be forced out of the bottom of the can via tubule 42 into the pressurized liquid line 11 of FIG. 2.

Figure 5:
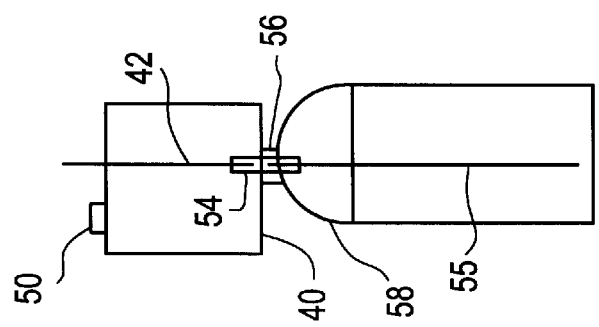
FIG. 5 is a schematic diagram showing an alternative variant of the water supply 10.

More details of can 40 are shown in FIG. 5. A cap 50 at the top of the can permits refilling of the water supply between dental treatments. A threaded fixture 56 at the bottom of can 40 permits an opening within the fixture to be either capped for use with a limited volume of water, e.g., about a cup-full, or to substantially enlarge the total water supply by attaching a sleeve 54 with an extension tubule 55 to tubule 42 and by threading the neck of a commercial 1-liter soft-drink bottle 58, such as that of Coca Cola or Pepsi Cola, into the opening of fixture 56.

Figure 6:
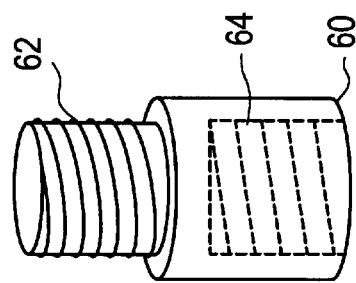
FIG. 6 is a schematic diagram of the adapter 56 of FIG. 5.

A schematic design drawing of fixture 56 is shown in FIG. 6. Here the fixture is made of a commercially available polyvinyl chloride pipe fitting 60 having external threads 62, which can be screwed into the bottom of can 40 of FIG. 5. Within the lower and larger portion of fitting 60 is embedded a bored cap from a commercial 1-liter soft drink bottle. The inner threads of the bored cap can then be mated with those on the neck of a soft drink bottle or of a threaded plug.

All the interconnections between the components of FIGS. 1–5 and the pressurized lines 3, 5, 7, 9, 11, 13, and 15 are preferably of the quick connect and disconnect type, which facilitates rapid disassembly or reassembly of the equipment for operation in various locations. Following dental work, the entire system can be quickly disassembled and fitted within a carrying case for easy transportation.

From the foregoing, it can be seen that there has been provided a simple, convenient to use, and inexpensive portable dental apparatus for treating indigenous populations in remote areas or for veterinary dentistry.

There will now be obvious many variations and modifications of the afore-disclosed embodiments to persons skilled in the art. All of these variations and modifications will remain within the scope of this invention if defined by the following claims.

I claim:

1. Portable dental drilling and bone cutting apparatus for treating patients or animals in remote locations comprising:
   a dental drill driven by an air turbine;
   a pressurized air supply means for driving said turbine and for pressurizing a water supply means;
   means for cooling said drill with a stream of water from said water supply means; and
   means for squirting air or water from said air and water supply means,
   wherein said pressurized air supply means derives its air from a manual pumping means,
   wherein said pumping means forms part of said air supply means; and
   wherein said manual pumping means comprises a check valve for minimizing fluctuations in the air flow rate.

2. The apparatus of claim 1, wherein said manual pumping means comprises a double-action pump.

3. The apparatus of claim 2, wherein said air supply means comprises a second manual pumping means.

4. The apparatus of claim 2, comprising also an inflatable container that has been filled by said pumping means.

5. The apparatus of claim 1, wherein said air supply is an inflatable container that has been filled by said pumping means.

6. The apparatus of claim 1, comprising valving means for controlling the flows of air and water through said drill and squirting means and quick disconnect and connect tubing between said air supply means, valving means, water supply means, drill, and squirting means to facilitate assembly and disassembly of said apparatus.

7. The apparatus of claim 1, wherein said water supply means comprises a can with a capped opening at or near its top for replenishing with water as needed, a tubule extending from the inside of said can near its base to above the top of the can, and a threaded opening in the can in or near its base into which is screwed an adapter that can be either plugged or used to enlarge the capacity of the water supply means.

8. The apparatus of claim 7, wherein the cap from a soft-drink bottle with a hole through its top is fitted into said adapter so as to permit affixing either a bottle or a plug to said can in or near its base.

9. The apparatus of claim 8, comprising extension means for attaching to said tubule a second tubule extending through the hole in said cap so as to nearly reach the bottom of said bottle when the bottle is affixed to said can.

10. A method of performing dental work on patients or animals in remote locations comprising the steps of:
   generating pressurized air by manual pumping;
   feeding said pressurized air to an air turbine for driving a dental drill;
   feeding said pressurized air to a water supply means for pressurizing said water;
   cooling said drill with a stream of water from said water supply means; and
   squirting air or water with said pressurized air and said pressurized water through a squirting means.

11. The method of claim 10, wherein said pumping is effectuated with a double-action pump.

12. The method of claim 10, wherein the pressurized air that is generated by said manual pumping is first fed to an inflatable container and is subsequently fed from said container to said turbine, water supply means, and squirting means.

13. The method of claim 10, comprising the preliminary step of replenishing said water supply means with water before feeding said pressurized air thereto.

14. The method of claim 13, wherein said water supply means comprises a can with a capped opening at or near its top and wherein said preliminary replenishing step comprises removing the cap so as to expose said opening, pouring water through said opening, and resealing said opening by recapping it.

15. The method of claim 14, comprising the additional preliminary steps of providing a threaded opening In or near the base of said can and screwing into said opening an adapter that can be either plugged or used to enlarge the capacity of the water supply means.

16. The method of claim 15, comprising the additional preliminary steps of boring a hole through the top of a cap from a soft-drink bottle and fitting the bored cap into said adapter so as to permit affixing either a bottle or a plug to said can at or near its base.

17. The method of claim 16, comprising the additional preliminary steps of providing a first tubule extending from the inside of said can near its base to above the top of the can and extension means for connecting to said tubule a second tubule extending through the hole in said cap and nearly reaching the bottom of said bottle when the bottle is affixed to said can.

18. The method of claim 10, comprising the additional preliminary steps of providing valving means and quick connect and disconnect tubing for controlling the flows of air and water through said drill and squirting means and to facilitate assembly and disassembly of said air and water supply means.

\* \* \* \* \*